United States Patent [19]

Lee

[11] Patent Number: 5,763,399

[45] Date of Patent: Jun. 9, 1998

[54] COMPOSITION AND METHOD FOR REVITALIZING SCAR TISSUE

[75] Inventor: Clarence C. Lee, Lilburn, Ga.

[73] Assignee: C.R. Bard, Inc., Murray Hill, N.J.

[21] Appl. No.: 465,141

[22] Filed: Jun. 5, 1995

Related U.S. Application Data

[62] Division of Ser. No. 183,628, Jan. 19, 1994, abandoned, which is a continuation of Ser. No. 15,275, Feb. 8, 1993, abandoned, which is a continuation of Ser. No. 728,171, Jul. 10, 1991, abandoned.

[51] Int. Cl.$^6$ .............................. A61K 38/08; A23J 1/10; C08H 1/06
[52] U.S. Cl. .................... 514/12; 424/426; 424/85.1; 424/520; 530/356; 514/21
[58] Field of Search .................. 514/12, 21; 530/351, 530/399; 424/520

[56] References Cited

U.S. PATENT DOCUMENTS

| Re. 33,375 | 10/1990 | Luck et al. ................................ 514/2 |
|---|---|---|
| 4,061,731 | 12/1977 | Gottleib .................................. 424/101 |
| 4,167,945 | 9/1979 | Gottlieb .................................. 424/101 |
| 4,191,751 | 3/1980 | Gottlieb .................................. 424/101 |
| 4,582,640 | 4/1986 | Smestad et al. ......................... 514/12 |
| 4,703,108 | 10/1987 | Silver et al. ............................. 530/356 |
| 4,760,131 | 7/1988 | Sundsmo et al. ....................... 530/356 |
| 4,774,091 | 9/1988 | Yamahira et al. ...................... 424/426 |
| 4,810,693 | 3/1989 | Pickart .................................... 514/18 |
| 4,840,940 | 6/1989 | Sottiurai ................................. 514/56 |
| 4,849,141 | 7/1989 | Fujioka et al. ......................... 264/211.11 |
| 4,861,757 | 8/1989 | Antoniades et al. .................... 514/21 |
| 4,952,403 | 8/1990 | Vallee et al. ............................ 424/422 |
| 4,952,404 | 8/1990 | Vallee et al. ............................ 424/422 |
| 4,970,298 | 11/1990 | Silver et al. ............................. 530/356 |
| 5,162,430 | 11/1992 | Rhee et al. .............................. 525/54.1 |
| 5,196,185 | 3/1993 | Silver et al. ............................. 424/45 |
| 5,258,028 | 11/1993 | Ersek ...................................... 623/11 |

FOREIGN PATENT DOCUMENTS

WO 90/03797  4/1990  WIPO.

OTHER PUBLICATIONS

"Wound Repair" by Jeffrey M. Davidson in Inflammation: Basic Principles and Clinical Correlation, 2nd ed., Raven Press, 1992 pp. 809–819.

Benharroch, D., et al., "Biology of the Fibrblast Growth Factor Gene Family," ISR. J. Med. Sci., vol. 26, pp. 212–219 (Apr. 1990).

Clark, R.A., "Cutaneous Tissue Repair: Basic Biologic Considerations," J. Am. Academy Dermat., vol. 13, pp. 701–725 (Nov. 1985).

Cooper, M.L., et al., "Use of a Composite Skin Graft Composed of Cultured Human Keratinocytes and Fibroblasts and a Collagen–GAG Matrix to Cover Full–Thickness Wounds on Athymic Mice," Surgery, vol. 109, pp. 198–207 (Feb. 1991).

Fajardo, L.F., et al., "Methods in Laboratory Investigation: The Disc Angiogenesis System," Lab. Invest. vol. 58, 718–724 (Jun. 1988).

Gore, D.C., et al., "Effect of Exogenous Growth Hormone on Whole–Body and Isolated–Limb Protein Kinetics in Burned Patients," Arch. Surg., vol. 126, pp. 38–43 (Jan. 1991).

Grotendorst, G.R., et al., "EGF and TGF–alpha are Potent Chemoattractants for Endothelial Cells and EGF–like Peptides and Present at Site of Tissue Regeneration," J. Cell Physio., vol. 139, pp. 617–623 (Jun. 1989).

Hansson, H.A., et al., "Transient Expression of Insulin–Like Growth Factor I Immunoreactivity by Vascular Cells During Angiogenesis," Exp. Mole. Path., vol. 50, pp. 125–138 (Feb. 1989).

Hockel, M., et al., "Purified Monocyte–Derived Antiogenic Substance (Angiotropin) Induces Controlled Angiogenesis Associated with Regulated Tissue Proliferation in Rabbit Skin," J. Clin. Invest., vol. 82, pp. 1075–1090 (Sep. 1988).

Knighton, D.R., et al., "Wound Healing Angiogenesis: Indirect Stimulation by Basic Fibroblast Growth Factor," J. Trauma, vol. 30, pp. 134–144 (Dec. 1990).

Laato, M., "Effect of Epidermal Growth Factor (EGF) on Blood Flow and Albumin Extravasation in Experimental Granulation Tissue," Acta Chir. Scand., vol. 152, pp. 401–405 (1986).

Mahadevan, V., et al., "Facotrs Influencing Blood Supply in Wound Granuloma Quantitated by New in Vivo Technique," Cancer Res., vol. 49, pp. 415–419 (Jan. 15, 1989).

Pierce, G.F., et al., "Platelet–derived Growth Factor (BB Homodimer), Transforming Growth Factor–β1, and Basic Fibroblast Growth Factor in Dermal Wound Healing," Am. J. Path., vol. 140, No. 6, pp. 1375–1388 (Jun. 1992).

Qian, J.J., et al., "Increased Cell Attachment, Migration and Differentiation on Hydroxyapatite in the Presence of a Collagen–Analog," Transactions of the Society for Biomaterials, 216 (1994).

Reilly, W., et al., "Matrix Control of Tumer Angiogenesis," Adv. Exp. Med. and Biol., vol. 242, pp. 211–227 (1988).

Savage, K., Ph.D., "The Effect of Platelet–Derived Growth Factor on Cell Division and Glycosaminoglycan Synthesis by Human Skin and Scar Fibroblasts," The J. Invest. Derm., vol. 89, pp. 93–99 (1987).

Tsuboi, R., et al., "Recombinant Basic Fibroblast Growth Factor Stimulates Wound Healing In Healing–Impaired db/db Mice," J. Exp. Med., vol. 172, pp. 245–252 (Jul. 1990).

Valettte, G., et al., "Une Nouvelle Methode d–Assai Des Traitments Cicatrisant FondéSur La Mise En Oeuvre D'une Plaie Expérimentals Dont La Cicatrisation Est Artificiellement Pertubée Par Hyperstimulation Locale Du Tissue De Granulation," Arzneimittelforschung, vol. 19, No. 7, pp. 1121–1132 (1969).

Van Brunt, J. et al., "Growth Factors Speed Wound Healing," Bio/Technology, vol. 6, No. 1, pp. 25–30 (1988).

Primary Examiner—Cecilia J. Tsang
Assistant Examiner—P. Lynn Touzeau
Attorney, Agent, or Firm—Jones & Askew, LLP

[57] ABSTRACT

A composition and method are provided that are effective in revitalizing scar tissue by introducing a bioactive substance having angiogenic activity into the scar tissue. The bioactive substance can be introduced by itself, or it can be introduced into the scar tissue in a timed release form. The present invention is effective in treating stress urinary incontinence or localized muscular dysfunction.

10 Claims, No Drawings

COMPOSITION AND METHOD FOR REVITALIZING SCAR TISSUE

This is a division of application Ser. No. 08/183,628, filed Jan. 19, 1994, now abandoned, which is a continuation of application Ser. No. 08/015,275, filed Feb. 8, 1993, now abandoned, which is a continuation of Ser. No. 07/728,171, filed Jul. 10, 1991, now abandoned.

TECHNICAL FIELD

The present invention relates to a composition and method for revitalizing scar tissue. More particularly, the invention relates to a composition and method for treating localized muscular dysfunction due to scarring following surgery, irradiation, laceration, burns or infections by introducing a controlled release, bioactive substance having angiogenic activity into the scar tissue. Potential applications for this invention include, but are not limited to, treating urinary incontinence, dermal scars, vocal cord injury, and esophageal injury.

BACKGROUND OF THE INVENTION

The term "revitalize" as used herein means to restore vascularization and elasticity to tissue having been injured and scarred. The term "injury" as used herein means a wound caused by surgery, irradiation, laceration, toxic chemicals, viral infection or bacterial infection. The term "scar tissue" means fibrotic or collagenous tissue formed during the healing of a wound or other morbid process. Scar tissue is fibrotic tissue made up mostly of disorganized collagen fibrils and is formed following injury or inflammation of local tissues. The term "controlled release matrix" means any composition which will allow the slow release of a bioactive substance which is mixed or admixed therein. The matrix can be a solid composition, a porous material, or a semi-solid, gel or liquid suspension containing the bioactive substance. The term "implant" means introduction of the bioactive material/matrix by means of injection, surgery, catheters or any other means whereby the bioactive material is introduced into the scar tissue. The bioactive material and matrix can also be implanted or injected proximate to the scar tissue so long as a significant amount of the bioactive material is able to enter the scar by direct diffusion to induce the angiogenic process into the scar. The term "bioactive material" means any angiogenic composition that will promote vascularization and revitalization of scar tissue when used in accordance with the present invention.

Scar tissue is fibrotic tissue composed mostly of disorganized collagen fibrils. It is tissue that is poorly vascularized, poorly innervated, and inelastic. Due to its lack of innervation and inelasticity, scar tissue is readily susceptible to repeated injury. After injury, scar tissue is slow to heal because of its poor vascularization.

When the normal cellular elements and extracellular matrix of damaged tissue are replaced by a distorted accumulation of scar tissue, the normal function of the tissue is lost. The formation of scar tissue can create localized muscular dysfunctions or inhibit a variety of physiological functions. A scar that causes deformity or impairs the function of an extremity is termed a "vicious cicatrix." For example, many male patients suffering from urinary incontinence have had prostectomies. Many female urinary incontinent patients have also been treated surgically or with irradiation prior to the development of incontinence. Surgery and irradiation tend to leave residual scar tissue at the site which has been irradiated or near anastomoses. The scar tissue which replaces normal periurethral tissue reduces tissue elasticity and causes incomplete urethral coaptation which can inhibit bladder control, resulting in incontinence.

Physicians have attempted to stretch and bulk scar tissue to restore the physiological function of the tissue by injecting inert materials, such as collagen and Teflon® paste, into the scar. However, because scar tissue is hard and inelastic, it cannot accommodate a large quantity of biomaterial. Injection of inert material into the scar tissue will stretch and bulk the scar tissue slightly, but eventually leakage results. Furthermore, the inert materials injected into the scar tissue increase the mass of the scar tissue, but they do not increase the elasticity of the tissue because they do not promote vascularization or infiltration of fibroblasts.

Researchers have focused primarily on developing methods and compositions which promote wound healing and minimize scarring and associated problems, rather than revitalize the scar tissue itself. For example, a patent issued to Gottlieb, U.S. Pat. No. 4,191,751, discloses a method for promoting the growth of new connective tissue over a surface wound wherein at least a portion of the epithelium has been damaged or removed. The patent describes a composition comprising finely-divided collagen and fibrin stabilizers which is applied to a surface wound to promote the growth of new connective tissue over the surface wound.

As another example, the patent to Gottlieb, U.S. Pat. No. 4,167,945, discloses a method for grafting a surface of donor tissue to a recipient tissue surface comprising the steps of coating a freshly exposed recipient tissue surface with the composition disclosed in Gottlieb '751. Neither patent discloses introducing the composition into scar tissue or using the composition to revitalize scar tissue.

Implants of similar compositions have previously been used to promote healing. Two patents issued to Vallee et al., U.S. Pat. Nos. 4,952,403 and 4,952,404, disclose the use of bioactive implants to promote the healing of avascular tissue by providing an effective dose of an angiogenic factor in proximity to the injured tissue. The tissues listed in the patents include fibrocartilage, such as the meniscus of the knee or the wrist, or the end of the clavicle, or of the temporomandibular joint, all of which are resistant to vascularization after either accidental injury, such as laceration or tearing, or after deliberate surgical incision. Specifically, Vallee '403 is directed to a composition comprising an angiogenic peptide and a pharmaceutically acceptable carrier and Vallee '404 is directed to a method of promoting healing of avascular tissue of a meniscus by implanting the composition comprising an angiogenic peptide and a pharmaceutically acceptable carrier. Neither patent discloses revitalizing scar tissue for the purpose of treating incontinent patients by injecting active biomaterials which would promote revascularization and fibroblast infiltration into the scar tissue.

Implants of inert biomaterials have previously been used for improving the appearance of scar tissue. In a patent issued to Gottlieb, U.S. Pat. No. 4,061,731, use of an implant of inert biological material to correct the appearance of a scar is described. Gottlieb '731 discloses compositions useful for the repair of depressed cutaneous scars that are characteristic of *acne vulgaris*. These compositions include finely-divided collagen and fibrin stabilizers such as gelatin sponge, aminocaproic acid and $4NH_2CH_2(CH_2)_4COOH-CaX_2$. The compositions are injected beneath the acne scar. The motivation behind the invention disclosed in Gottlieb '731 is to build up or bulk the tissue under an acne scar, thereby reducing the depression caused by the scar. The inert material injected into the scar does not revitalize the scar tissue.

Implants of inert matrices containing cytotoxic drugs have also been used to treat abnormal cellular growths. The patent issued to Luck, U.S. Pat. No. Re. 33,375, discloses a proteinaceous composition of collagen or fibrinogen containing a cytotoxic drug or a proliferation inhibitor. Luck is directed to a method of treating cellular disorders involving abnormal cellular growths by introducing the proteinaceous composition of collagen or fibrinogen containing a cytotoxic drug or a proliferation inhibitor at the site of the disorder. Luck does not disclose the revitalization of scar tissue for the purpose of treating incontinence by applying bioactive materials to or into the scar tissue.

A method of preparing biodegradable collagen-based materials in sponge or sheet form is disclosed in Silver et al., U.S. Pat. No. 4,703,108. Silver describes using the matrix for short term drug release in internal wounds but does not describe using the matrix to revitalize scar tissue.

Patents issued to Yamahira et al., U.S. Pat. No. 4,774,091, and Fujioka et al., U.S. Pat. No. 4,849,141, describe methods of preparing sustained release biodegradable formulations. Yamahira '091 discloses a solid sustained-release preparation in the form of a needle-like or bar-like shape which consists essentially of an active ingredient and a pharmaceutically acceptable biodegradable carrier. These carriers can be proteins such as collagen or gelatin, and mixtures thereof. Yamahira '091 describes various active ingredients which can be used in the described invention including tissue plasminogen activator, prostaglandins, prostacyclines, various bio-hormones, interferons, interleukins, tumor necrosis factor and some other cytokines. However, Yamahira '091 does not teach revitalizing scar tissue in incontinent patients by injecting biomaterials which promote the revascularization of the scar tissue. In fact, Yamahira '091 teaches preparing a solid sustained-release preparation in the form of a needle or bar shape. It would be difficult to inject such a device into a solid tissue such as scar tissue.

Fujioka '141 discloses a method for preparing a sustained released formulation utilizing collagen and/or gelatin as a carrier, similar to the invention disclosed in Yamahira '091. Fujioka '141 discusses a time release formulation that has a variety of sizes and shapes including a liquid suspension of powder in a suitable solvent. However, there is no discussion in Fujioka '141 of treating incontinent patients by injecting bioactive biomaterials which promote the revascularization of the scar tissue.

The prior art discloses a wide variety of time release compositions for the slow release of various biologically active compounds. These methods and compositions are primarily directed towards either promoting healing of injured tissue or killing or inhibiting the growth of unwanted cells, such as cancer cells. However, the compositions and methods of the prior art do not address revitalization of scar tissue. Thus, there is a need for a composition and method of treating established scar tissue to alleviate its physiologically limiting effects and to restore at least a degree of normal function to the tissue. There is also a need for a composition and method of treating urinary incontinence resulting from the development of periurethral scar tissue.

SUMMARY OF THE INVENTION

In accordance with the present invention, a composition and method is provided that is effective in revitalizing scar tissue. The present invention is effective in treating localized muscular dysfunction resulting from scarring. The present invention is also effective in treating stress urinary incontinence.

The present invention embodies injecting into or proximate to scar tissue a composition comprising a bioactive material immobilized in a matrix for controlled release. Release of immobilized bioactive material into the scar tissue promotes vascularization of the tissue. The release of bioactive material can be slow or fast, depending upon the nature of the scar tissue. Eventually, the implant and the scar tissue is vascularized and infiltrated by fibroblasts, or the implant is replaced by blood vessels or fibroblasts thereby making the scar tissue more elastic and normal. For example, by revitalizing the scar tissue after a prostectomy, incontinence can be minimized.

The present invention can be used in any condition wherein the revascularization of scar tissue is desired. This includes treatment of scar tissue after surgery or injury to the gastrointestinal tract, epidermis, cardiac muscle, or other organs. The present invention can also be used to treat vascular and nerve scars or dysfunction.

Bioactive materials that can be used in the present invention include, but are not limited to, growth hormones, growth factors, biologically active segments of growth factors, angiogenic compositions, polysaccharides, or mixtures thereof.

Accordingly, it is an object of the present invention to provide a composition and method useful for revitalizing scar tissue.

It is a further object of the present invention to provide a method for revascularizing damaged tissue.

It is another object of the present invention to provide a composition which promotes infiltration of fibroblast cells into damaged tissue.

It is another object of the present invention to provide a composition in which bioactive material injected into tissue would have a longer half-life within the scar tissue.

It is another object of the present invention to provide a composition and method for treating rectal incontinence.

It is another object of the present invention to provide a composition and method for treating scarring of voice cords.

It is another object of the present invention to provide a composition and method for treating scar tissue in the esophagus and esophageal sphincters.

It is another object of the present invention to provide a composition in which the activity of the biomodulators are site-specific and adverse systemic effects are minimized.

It is another object of the present invention to provide a method useful for treating muscular dysfunctions caused by the accumulation of scar tissue.

It is another object of the present invention to provide a method useful for treating dysfunctions caused by the accumulation of scar tissue.

It is another object of the present invention to provide a method useful for treating stress urinary incontinence.

It is a further object of the present invention to provide a method for treating urinary incontinence following prostectomy or irradiation.

It is another object of the present invention to provide a method useful for treating impotence caused by the accumulation of scar tissue.

These and other objects, features, and advantages of the present invention will become apparent after a review of the following detailed description of the disclosed embodiments and the appended claims.

DETAILED DESCRIPTION

In accordance with the present invention, a composition and method are provided that are effective in revitalizing scar tissue. The present invention is effective in treating dermal scars, stress urinary incontinence, vesicoureteral reflux, rectal incontinence, esophageal scarring, esophageal sphincter scarring, scarring of the voice cords, or localized muscular dysfunction. The present invention can also be effective in treating hardened capsules usually formed around foreign-body implants such as mammary implants, penile implants, and artificial urinary sphincters.

Revascularization and introduction of normal cellular elements, such as fibroblast cells, to scars can actually "revitalize" the tissue, i.e., expand, soften, and restore elasticity to the hardened scars. For example, in the case of urinary incontinence caused by periuretheral scar tissue, by repeating the injection of specific bioactive biomaterials, the scar tissue can be expanded to achieve urethral coaptation and relieve the incontinence. Alternatively, the bioactive material can be incorporated into a delivery substance for slow release into the scar tissue, thereby reducing the required number of injections.

The present invention comprises a composition which will slowly release a bioactive material, thereby promoting the vascularization and infiltration of fibroblasts into the scar tissue. The composition generally comprises a matrix which will allow the slow release of a bioactive material that is incorporated therein.

The present invention also comprises the step of injecting into or proximate to scar tissue a composition which will slowly release a bioactive material, thereby promoting the vascularization and infiltration of fibroblasts into the scar tissue. The composition generally comprises a matrix which will allow the slow release of a bioactive material that is incorporated therein.

It is to be understood that the phrase "injecting into" means injecting the bioactive material either into a scar tissue or proximate to the scar tissue.

In addition, it is contemplated as part of the present invention the step of injecting bioactive materials directly into or proximate to scar tissue without a matrix carrier. If the bioactive materials are injected directly into or proximate to scar tissue, multiple injections will be required. The number of injections will depend upon how fast the scar tissue is revitalized. The bioactive material is dissolved in an appropriate buffer at a dose that is effective in revitalizing the scar tissue.

Examples of bioactive materials which can be used in the present invention include, but are not limited to: (1) pituitary or synthetic growth hormones, (2) growth factors, (3) active fragments of growth factors, (4) fibronectin, (5) materials composed of a matrix and growth factors (or active segments of growth factors), (6) interleukins, and (7) materials or synthetic compounds which promote the revascularization and infiltration of fibroblast cells into the scar tissue. Pituitary growth hormones, both natural or synthetic, have broad effects on various organs and tissues. Generally speaking, a growth factor has more specific biological effects on limited types of cells, tissues or organs which possess the corresponding cell surface receptor. For example, nerve growth factor induces the regeneration of peripheral nerve cells. (For a general review of angiogenisis, please see Maciag, T., *Molecular and Cellular Mechanisms of Angiogenesis*, IMPORTANT ADV. ONCOL., pp. 85–98, 1990.) Mixtures of different bioactive materials can be used in practicing the present invention.

Specific examples of bioactive materials which can be used with the present invention include, but are not limited to, pituitary growth hormones (hGH and bGH) and various growth factors such as fibroblast growth factors (FGF), insulin-like growth factors (IGF), platelet-derived growth factors (PDGF), and transforming growth factors, including transforming growth factor alpha and beta. The bioactive materials which can be used with the present invention also include active peptide segments of various growth factors, e.g., binding site peptides (or dormants) of growth factors, which bind the receptors of fibroblast or other cells. Bioactive materials also include angiogenic synthetic peptides having biological activities similar to growth factors. Gly-His-Lys (GHK), Gly-Arg-Gly-Asp (GRGD) and Arg-Gly-Asp (RGD) are examples of synthetic peptides.

Additionally, vitamin A and complexes of copper ions chelated by peptides, polysaccharides or organic chelating agents, or other compounds, can also act as bioactive materials. Any of the above mentioned bioactive materials can be used alone or as mixtures thereof.

It is to be understood that the selection of bioactive material is not critical to the present invention. It is well within the knowledge of one of ordinary skill in the art to select suitable angiogenic substances to practice the present invention.

Suitable biodegradable matrices that can be used in the present invention include, but are not limited to, collagen, gelatin, albumin, chondroitin sulfate, hyaluronic acid, heparin, oxidized cellulose, dextran, polyglycolic acid, polylactic acid, polyanhydride, or the like.

Bioactive materials can also be cross-linked to each other to serve as their own matrix for controlled release purposes. These substances can be used alone or in any combination of two or more thereof. Methods of preparing biodegradable matrices can be found in U.S. Pat. No. 4,774,091, U.S. Pat. No. 4,703,108, and U.S. Pat. No. 4,849,141, all of which are incorporated herein by reference.

When the matrix is degraded by the body, the active components are gradually released. Simultaneously, angiogenesis, fibroblast infiltration, collagen production, proteoglycan production, and chemoattractant activity increase at the implant site.

Non-biodegradable matrices can also be used in the present invention. When a non-biodegradable matrix is used according to the present invention, the composition with the bioactive material distributed in the non-biodegradable matrix is injected into the scar tissue. The bioactive material then diffuses out of the matrix, thereby causing vascularization of the scar tissue. Non-biodegradable carriers include compounds such as Dacron®, polyethylene glycol diacrylate polymers, silicone, porous metals, polyHEMA™, polyurethane, polyethylene, and polycarbonate, among others.

The preferred matrices for use in the present invention are the biodegradable matrix comprising collagen, gelatin, albumin, chondroitin sulfate, hyaluronic acid, heparin, oxidized cellulose, dextran, polyglycolic acid, polylactic acid, polyanhydride, or a mixture thereof. Collagen is a protein derived from connective tissue of animals. It has less antigenicity than many other proteins and hence has been used widely in human applications. Gelatin, a protein derived from collagen, is a high molecular weight protein which has the property of being convertible between liquid and gel forms. Gelatin has also been used extensively in human therapeutic applications.

The bioactive materials are immobilized in a matrix to allow sustained release and site specific action. The bioactive materials may be either covalently bonded to the matrix or ionically bonded to the matrix. The matrix itself can be either a biodegradable polymer/biopolymer or a nondegradable polymer. The covalent cross-linkers can be any of bi-functional cross-linking molecules, including, but not limited to, gluteraldehyde, divinylsulfone, diisocyanate, cyanogen bromide activated cellulose, and 1, 1 carbonyl dimidazol activated polyethylene glycol. The covalent cross-linking bonds between the bioactive material and the matrix or between bioactive molecules can also be formed by UV or gamma irradiation. The bioactive materials can be immobilized by ionic coupling to a matrix or to themselves. The bioactive materials can also be encapsulated with or without covalent and/or ionic bonds. One example is the liposome encapsulated insulin-like growth factor. Bioactive materials can also be cross-linked to each other for sustained release.

The preferred method of introducing the controlled release composition comprising matrices containing bioactive materials is by injection. The controlled release composition is injected preferably at multiple sites until the scar tissue is uniformly infiltrated with the controlled release composition. Usually, the controlled release composition needs to be administered only once. However, in some cases, a second or third administration may be necessary to achieve desired results. The controlled release composition may also be administered by implanting the composition surgically when injection is not practical.

In a preferred embodiment of the present invention, human growth hormone (hGH) is injected locally into periurethral tissues at or near pelvic floor muscles, using the controlled release mechanism described above, to treat stress urinary incontinence. hGH stimulates the synthesis of chondroitin sulfate and collagen as well as the excretion of hydroxyproline. The dose of human growth hormone will depend upon the source of the protein but is easily determined by one of ordinary skill in the art.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

An example of utilizing a biodegradable matrix for delivery of a bioactive substance to scar tissue is provided. A biodegradable matrix comprising human albumin-heparin microspheres is prepared from albumin-heparin conjugates (Hennick et al., "Covalently Bound Conjugates and Albumin and Heparin: Synthesis, Fractionation and Characterization", *Throm. Res.*, Vol. 29, pp. 1–13, 1983) as described by Tomlinson et al., ("Human Serum Albumin Microspheres for Intraarterial Drug Targeting of Cytostatic Compounds, Pharmaceutical Aspects and Release Characteristics," in: S. S. Davis et al., eds., *Microspheres and Drug Therapy, Pharmaceutical, Immunological and Medical Aspects*, Elsevier, Amsterdam, pp. 75–89, 1984). Next, human growth hormone (hGH; somatotropin) is incorporated into the human albumin-heparin microsphere matrix by mixing approximately 50 mg of the microspheres and 5 mg of hGH in buffer. 0.5 ml of 0.1% (wt./wt.) gluteraldehyde in 4.5 ml of buffer is added to the mixture while mixing gently. The mixture is gently mixed at 4° C. overnight. The reaction of aldehyde is terminated with 50 ml of 0.1% lysine. Approximately 5 ml of the suspension is then injected into the target tissue at multiple sites until the target tissue is uniformly impregnated with the controlled release composition.

EXAMPLE 2

An example of utilizing a non-biodegradable matrix for delivery of the bioactive substance to scar tissue is provided. A porous silicon bead matrix is plasma treated to introduce —OH groups for the immobilization of insulin-like growth factor. 50 mg of insulin-like growth factor is added to a mixture of 5 g of beads in 15 ml of water. The mixture is de-areated under vacuum. Approximately 10 ul of diisocyanate is added to the mixture while stirring. The mixture is stirred for 1 hour at room temperature. The beads are washed with 50 ml of saline solution 5 times. 5 g of beads are then suspended in 10 g glycerol. Approximately 2 g of the suspension is implanted in the scar tissue at multiple sites until the target tissue is uniformly impregnated with the controlled release suspension.

It should be understood, of course, that the foregoing relates only to a preferred embodiment of the present invention and that numerous modifications or alterations may be made therein without departing from the spirit and the scope of the invention as set forth in the appended claims.

What is claimed is:

1. A composition for revitalizing pre-existing scar tissue in a human or animal comprising a naturally occurring growth factor and a biodegradable matrix, wherein the composition revitalizes the pre-existing scar tissue when injected into the pre-existing scar tissue, and wherein the biodegradable matrix is not collagen.

2. The composition of claim 1, wherein the biodegradable matrix is selected from the group consisting of hyaluronic acid, alginate, agarose, and dextran.

3. The composition of claim 1, wherein the naturally occurring growth factor is fibronectin.

4. The composition of claim 1, wherein the naturally occurring growth factor is an active peptide segment capable of binding to fibroblast receptors.

5. The composition of claim 1, wherein the naturally occurring growth factor is growth hormone.

6. The composition of claim 1, wherein the naturally occurring growth factor is insulin-like growth factor.

7. The composition of claim 1 wherein the naturally occurring growth factor is platelet-derived growth factor.

8. The composition of claim 1, wherein the naturally occurring growth factor is transforming growth factor.

9. The composition of claim 8, wherein the growth factor is transforming growth factor beta.

10. The composition of claim 8, wherein the growth factor is transforming growth factor alpha.

* * * * *